United States Patent
Heng

[11] Patent Number: 5,865,722
[45] Date of Patent: Feb. 2, 1999

[54] SHAPE-ADAPTABLE TOPICAL HYPERBARIC OXYGEN CHAMBER

[75] Inventor: Madalene C. Y. Heng, Northridge, Calif.

[73] Assignee: Numotech, Incorporated, Sun Valley, Calif.

[21] Appl. No.: 832,956

[22] Filed: Apr. 4, 1997

[51] Int. Cl.$^6$ .................................................. A61M 13/00
[52] U.S. Cl. ........................................................... 600/21
[58] Field of Search ......................... 600/21; 128/202.12; 604/205.26, 23, 293; 5/706; 251/145

[56] References Cited

U.S. PATENT DOCUMENTS

| | | |
|---|---|---|
| 2,832,336 | 4/1958 | Davis et al. . |
| 3,186,404 | 6/1965 | Gardner . |
| 3,450,450 | 6/1969 | Hopkins et al. ............... 128/202.12 X |
| 3,602,221 | 8/1971 | Bleicken . |
| 3,744,491 | 7/1973 | Fischer . |
| 3,754,731 | 8/1973 | Mackal et al. ........................... 251/145 |
| 4,003,371 | 1/1977 | Fischer ..................................... 604/23 |
| 4,474,571 | 10/1984 | Lasley . |
| 4,509,513 | 4/1985 | Lasley ................................. 128/202.12 |
| 4,772,259 | 9/1988 | Frech ........................................ 604/23 |
| 4,801,291 | 1/1989 | Loori ......................................... 604/23 |
| 5,029,579 | 7/1991 | Trammell . |
| 5,109,837 | 5/1992 | Gamow ................................ 128/202.12 |
| 5,255,673 | 10/1993 | Cardwell et al. ................... 128/202.12 |
| 5,279,283 | 1/1994 | Dillon . |
| 5,312,385 | 5/1994 | Greco ....................................... 604/356 |
| 5,342,121 | 8/1994 | Koria ..................................... 600/21 X |
| 5,478,310 | 12/1995 | Dyson-Cantwell et al. .............. 604/23 |
| 5,542,414 | 8/1996 | Merilainen .......................... 128/204.22 |

*Primary Examiner*—John P. Lacyk
*Assistant Examiner*—Samuel Gilbert
*Attorney, Agent, or Firm*—Jack C. Munro

[57] ABSTRACT

A disposable hyperbaric oxygen chamber which is constructed of a flexible, thin-walled, polyethylene plastic bag which is of sufficient size to permit the entry of almost the entire body of an animal, most frequently that of a human, within the bag. The mouth of the bag is pleated so that the pleats can be bunched together into localized bulges to concentrate the volume of oxygen over the area of a wound such as a skin ulcer, lesion or injury. The wall of the bag includes at least one gas supply connector for connecting with a gas supply tube. The wall of the bag also includes a drain connector which is to be connected to a drain tube for removing of accumulated liquid within the internal chamber. The wall of the bag also includes at least one hand access opening which includes a thin-walled tubular glove member with this tubular glove member being locatable exteriorly of the wall of the bag or interiorly of the wall within the internal chamber. The caregiver's hand is to be connectable with the tubular glove member, and when the tubular glove member is located within the internal chamber of the bag, manual operations can be performed directly onto the body of the patient without breaking of the airtight environment of the internal chamber.

6 Claims, 3 Drawing Sheets

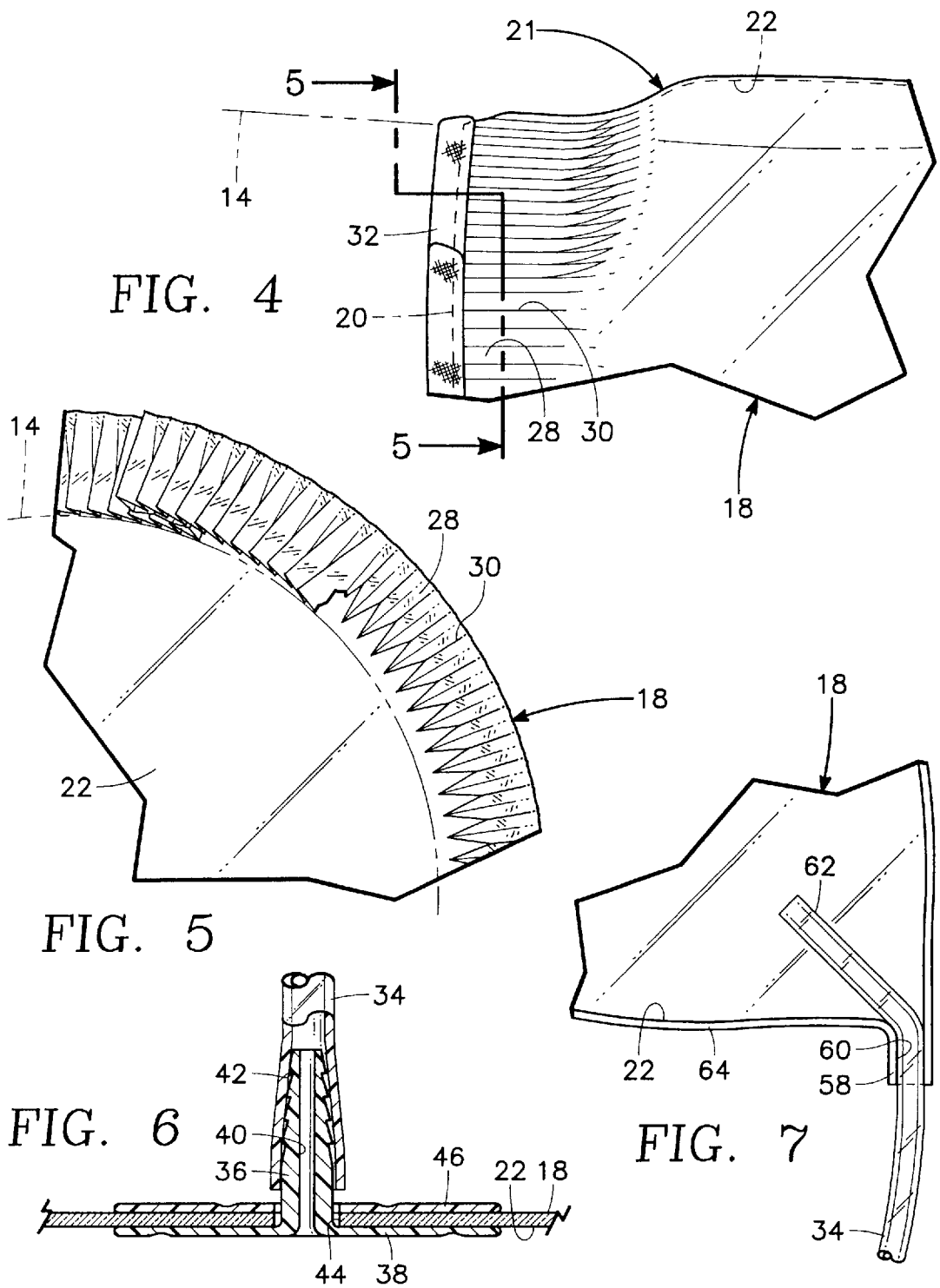

SHAPE-ADAPTABLE TOPICAL HYPERBARIC OXYGEN CHAMBER

BACKGROUND OF THE INVENTION

1) Field of the Invention

The present invention relates to a hyperbaric chamber and more particularly to a hyperbaric chamber for topically applied gas which includes oxygen which is portable and disposable and is designed to be used in connection with the torso and two or more limbs of an animal, such as a human body, creating a sealed environment for the application of oxygen containing gas to hasten healing of wounds such as skin ulcers, lesions and injuries on a patient's body.

2) Description of the Prior Art

Hyperbaric oxygen chambers have long been known. Hyperbaric oxygen chambers are for the purpose of introducing of pressurized oxygen into an encapsulated environment with this oxygen to promote the healing of various types of wounds. Specifically, it has been discovered that the treatment of wounds within an hyperbaric oxygen chamber promotes healing and suppresses bacterial infection.

When hyperbaric oxygen chambers were first introduced, such took the form of a rigid, heavy structure resembling an iron lung. The entire body of the patient, up to the neck of the patient, was placed within the chamber. One of the disadvantages of this type of hyperbaric oxygen chamber is that the patient had to be moved to the chamber. Also, because of the size and weight of the hyperbaric oxygen chamber, this type of hyperbaric oxygen chamber was quite expensive and therefore a typical hospital may only have one or two such chambers making it difficult to find the time to use the chamber(s) in conjunction with many different patients. Additionally, because of the possibility of transferred infection from one patient to another, time and effort had to be expended to clean the chamber between uses. All in all, such "iron lung" type of hyperbaric oxygen chambers were not convenient.

As time progressed, hyperbaric oxygen chambers became more sophisticated resulting in the production of a portable hyperbaric oxygen chamber. Not only was the hyperbaric oxygen chamber portable, it was inexpensive permitting the hyperbaric oxygen chamber to be disposed of after usage. These more sophisticated hyperbaric oxygen chambers came in various sizes some of which could basically encapsulate the entire torso of the patient or smaller versions of the chamber which would be used to encapsulate only small portions of the torso, such as an arm or a leg. However, the portable hyperbaric oxygen chambers of the prior art had certain shortcomings. One of the shortcomings is that it is important that the portable hyperbaric oxygen chamber assume a very loose fit around the patient's body so that a substantial volume of oxygen will be subjected to the wound. A close fit of the chamber to the body is undesirable. Many of the portable hyperbaric oxygen chambers of the prior art failed to adequately provide this type of loose fit.

Another shortcoming had to do with the connection of the gas supply tube to the chamber which may consist of a plastic bag. Frequently, the gas supply tube would have a tendency to kink right at the connection with the portable chamber which most often comprises a flexible thin-walled plastic bag. This kinking would result in diminishing or completely shutting off of the supply of gas into the internal chamber of the bag. In order for the hyperbaric chamber to work satisfactorily, a constant continuous supply of gas is required.

Another shortcoming of the prior art hyperbaric oxygen chambers is that at times a patient may be located in the chamber for a period of several hours, and this patient may even be unconscious. The patient may urinate. The prior art types of hyperbaric oxygen chambers were not constructed in a manner to facilitate the removal of the urine.

Another shortcoming of the prior art hyperbaric chambers is that there was no way to perform any kind of manual procedure on the patient through the wall of the chamber (bag). For example, sometimes it is necessary to move the patient or move a particular portion of the patient's anatomy from one location to another. Also, at times it is desirable to do some massaging to a particular area of the patient's body. Satisfactory contact with the patient's body is usually not possible with the prior art type of portable hyperbaric oxygen chambers because the wall thickness of the chamber is too great to facilitate manual procedures.

Another shortcoming is the lack of maintenance of the intrachamber pressures at a narrow range necessary for healing of skin ulcers, lesions and injuries. In order to maximize the growth of new blood vessels within the wound and retard the excessive formation of scar tissue, the pressures within the hyperbaric oxygen chamber must be maintained at all times within a narrow window of pressures within the chamber. Such a narrow "window" of pressure maintenance is not known in the prior art.

SUMMARY OF THE INVENTION

The present invention overcomes the deficiency of the prior art hyperbaric oxygen chambers and provides such a chamber for treating wounds which include skin ulcers, injuries and lesions. This chamber is disposable, portable, inexpensive, eliminates the possibility of kinking the bag at the gas supply tube that is connected to the chamber, permits the draining of any accumulated liquid within the chamber and also provides a way to perform physical operations on the patient's body while still maintaining a pressurized environment within the topical hyperbaric oxygen chamber. Most importantly, the hyperbaric oxygen chamber of this invention provides a way to ensure that the intrabag pressures are maintained at all times within the narrow "window" necessary to maximize the growth of new blood vessels while depressing the formation of excessive scar tissue. There is no known treatment to date that is capable of dissociating growth of scar tissue from growth of new blood vessels. The hyperbaric oxygen chamber of this invention utilizes an enclosing bag which is to have a single access opening. Substantially the entire torso (trunk) of the animal, which in most cases would be a human, is to be inserted within the internal chamber of the bag with the wall of the bag assuming a very loose fit in conjunction with the body of the human. Around the access opening of the bag, the wall of the bag is pleated to permit localized expansion of the bag in order to increase the volume of the internal chamber in the area directly over the wound. The wall of the bag has at least one supply connector which is connected to the gas source which includes oxygen. This supply connector has an enlarged flange and a tubular stem. This tubular stem is for connection with the oxygen supply tube. The enlarged flange is secured to the wall of the bag. This enlarged flange prevents pivoting of the connector relative to the bag which could result in kinking of the gas supply and the decreasing or not supplying of gas to the internal chamber of the bag. Also included within the wall of the bag is a drain connector, the function of which is to connect with a drain tube for removal of accumulated liquid within the internal chamber. Also formed within the wall of the bag will be at least one access opening for manipulating the patient while under treatment. Within this access/opening is a thin-walled glove.

This glove is readily flexible and is reversible by insertion of the hand of the caregiver into the glove. This will permit the caregiver to manipulate the patient within the sealed chamber.

One of the objectives of the present invention is to provide a hyperbaric oxygen chamber wherein the chamber itself is collapsible and can be stored in a substantially small amount of space prior to usage.

Another objective of the present invention is to construct a hyperbaric chamber which is inexpensive and disposable.

Another objective of the present invention is to provide a hyperbaric oxygen chamber which is light in weight so that it can be readily moved from a stowed position to the location of the patient rather than vice versa, and also the light weight achieves the advantage of minimal cost of shipping of the hyperbaric oxygen chamber to the medical facility.

Another objective of the present invention is to construct a hyperbaric oxygen chamber wherein the patient can move comfortably within the chamber and is not required to maintain a virtually rigid position for the time of treatment.

Another objective of the present invention is to construct a hyperbaric oxygen chamber which is basically transparent so that the body of the human can be readily viewed during the time of treatment.

Another objective of the present invention is that by constructing a hyperbaric chamber for topically applied gas which includes oxygen and which is disposable, there is eliminated the need for any cleaning of such chambers and also eliminates the transfer of infection which is a possibility when using such a chamber on multiple patients.

Another objective of the present invention allows for the incorporation of pressure sensors in conjunction with the chamber in order to maintain a narrow window of pressures that is necessary for maximizing growth of new blood vessels while at the same time suppressing the formation of scar tissue.

Another objective of the present invention is to construct the bag of the hyperbaric oxygen chamber to be readily changed in shape in order to accommodate and supply a substantial volume of gas to difficult locations of wounds on the body of the patient.

BRIEF DESCRIPTION OF THE DRAWINGS

FIG. 4 is an enlarged view of the body access opening of the thin-walled bag of the hyperbaric oxygen chamber showing more clearly the mounting and sealing of the bag onto the body of the patient with this view being taken along line 4—4 of FIG. 1;

FIG. 5 is a cross-sectional view through the pleated area of the bag located directly adjacent the body access opening taken along line 5—5 of FIG. 4;

FIG. 6 is an enlarged cross-sectional view through the first embodiment of gas connector which is mounted in conjunction with the wall of the bag taken along line 6—6 of FIG. 1;

FIG. 7 is a cross sectional view of a second embodiment of gas connector which is mounted in conjunction with the wall of the bag;

DETAILED DESCRIPTION OF THE PREFERRED EMBODIMENT

Figure 1:
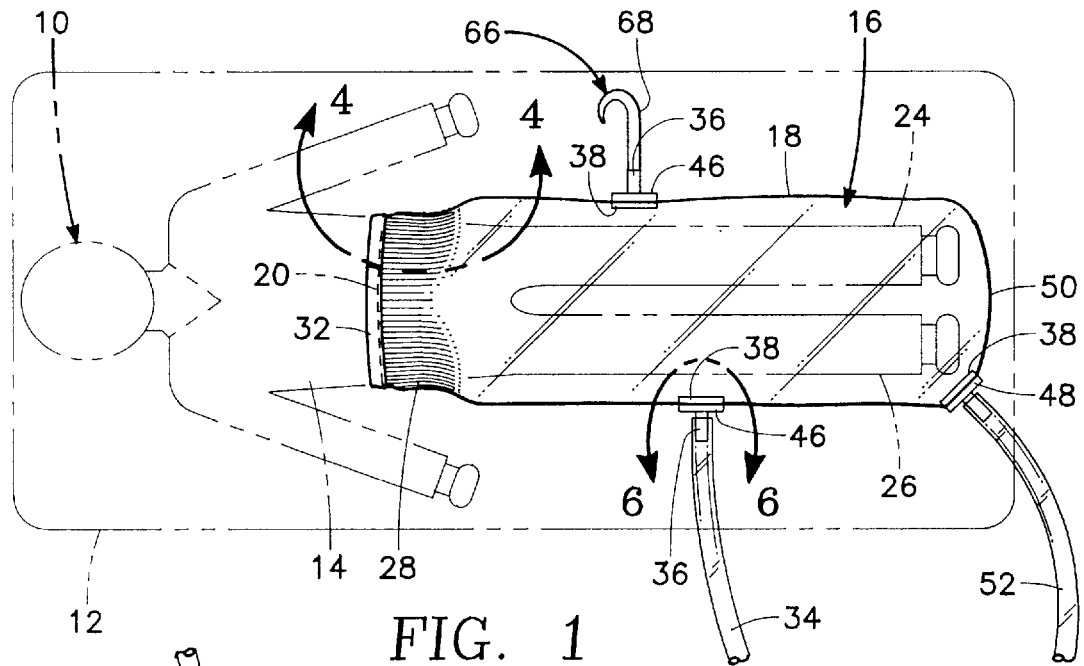
FIG. 1 is a top plan view of the hyperbaric oxygen chamber constructed in accordance with this invention showing such chamber (enclosing) being mounted on a typical human patient.

Referring particularly to the drawings, there is depicted a human 10 positioned in a prone position on a bed 12. The human 10 has a torso or trunk 14. A portable hyperbaric oxygen chamber 16 of the present invention is mounted in conjunction with the human 10 in the following manner.

The chamber 16 is primarily composed of an enlarged, sheet material plastic bag 18. A typical material of the bag 18 would be polyethylene. The bag 18 has a single access opening 20 which provides access into the internal chamber 22 of the bag 18. The access opening 20 is to be large enough that the legs 24 and 26 of the human 10 are to be locatable within the internal chamber 22 with the access opening 20 being positioned about the torso 14. It is important that the bag 18 be transparent.

The typical thickness of the bag 18 will generally be about 0.006 of an inch. The bag 18 directly adjacent to the access opening 20 includes a plurality of pleats 28. The pleats 28 are formed by a series of parallel, spaced apart score lines 30, with sections of the polyethylene folded upon itself, each fold being defined as a pleat. These pleats 28 facilitate the bunching up, overlapping or folding over of the pleats on each other so as to accommodate the different circumferences of the torso 14. Not only do the pleats 28 facilitate the adjustment to different sizes of torso 14, but also this overlapping of the pleats establishes a substantially close fit with the torso 14. The bag 18 in the area of the access opening 20 is filled around the torso 14 by means of a sealing tape 32. The sealing tape 32 is to be placed about the torso 14 and also about the access opening 20 of the bag 18 with the ends of the sealing tape 32 being secured to each other also in an overlapping arrangement. It is to be understood that the sealing tape 32 will include some kind of adhesive. As previously mentioned, there will be a certain amount of leakage of the pressurized gas mixture which includes oxygen, that is to be supplied within the internal chamber 22. This leakage will occur in the area of the sealing tape 32. It is desirable to have a small amount of leakage so that the gas contained within the internal chamber is constantly being changed.

Gas which includes oxygen is to be supplied from a source (not shown) through a gas supply tube 34 to within the internal chamber 22. The gas supply tube 34 is to be tightly mounted onto an upstanding connector stem 36 of a first embodiment of connector shown in FIGS. 1–3 and 6. The connector stem 36 is integral with an enlarged flange 38 with the flange being disc shaped and extending in a right angle outwardly from the stem 36. The connector stem 36 has a longitudinal through opening 40 and also a serrated exterior surface 42. The serrated exterior surface 42 will facilitate a snug fit with the gas supply tube 34. Also, the serrated exterior surface 42 will tend to resist disengagement of the gas supply tube 34 from the connector stem 36.

The connector stem 36 is to be inserted through a hole 44 formed within the bag 18. The flange 38 is to be located directly adjacent the interior surface of the bag 18. Mounted against the exterior surface of the bag 18 surrounding the connector stem 36 is a washer 46. Both the washer 46 and the flange 38 are to be tightly sealed to the bag 18. A typical method of sealing would be by means of heat.

It is the function of the connector stem 36, in conjunction with the flange 38 and the washer 46, to establish a non-kinking relationship between the bag 18 and the gas supply tube 34. Regardless of the position of the gas supply tube 34, there is to be always an open gas flow path between the gas supply tube 34 and the through opening 40, therefore, gas will always be free to flow from the gas supply tube 34 into the internal chamber 22.

Also mounted in conjunction with the bag 18 is a drain connector 48. The drain connector 48 is constructed in precisely the same way as the connector that is shown in FIG. 6 of the drawings. The drain connector 48 is mounted at the foot area 50 of the bag 18. Also, the drain connector 48 is to be located directly adjacent the bed 12. It is to be the function of the drain connector 48 to discharge any accumulated liquid within the internal chamber 22 into a drain hose 52. The liquid is to be discharged to an appropriate exterior discharge location which is not shown.

Formed within the wall surface of the bag 18 are a pair of hand access openings 54. Mounted in conjunction with each hand access opening 54 is a thin-walled, tubular member 56 which is constructed of rubber or plastic. The tubular member 56 is elongated and terminates at its outer end in the shape of a glove for a human hand. Each tubular member 56 establishes an airtight connection with the its respective hand access opening 54. One tubular member 56 is designed to accommodate the medical practitioner's left hand with the other tubular member 56 being designed to accommodate the medical practitioner's right hand.

Figure 2:
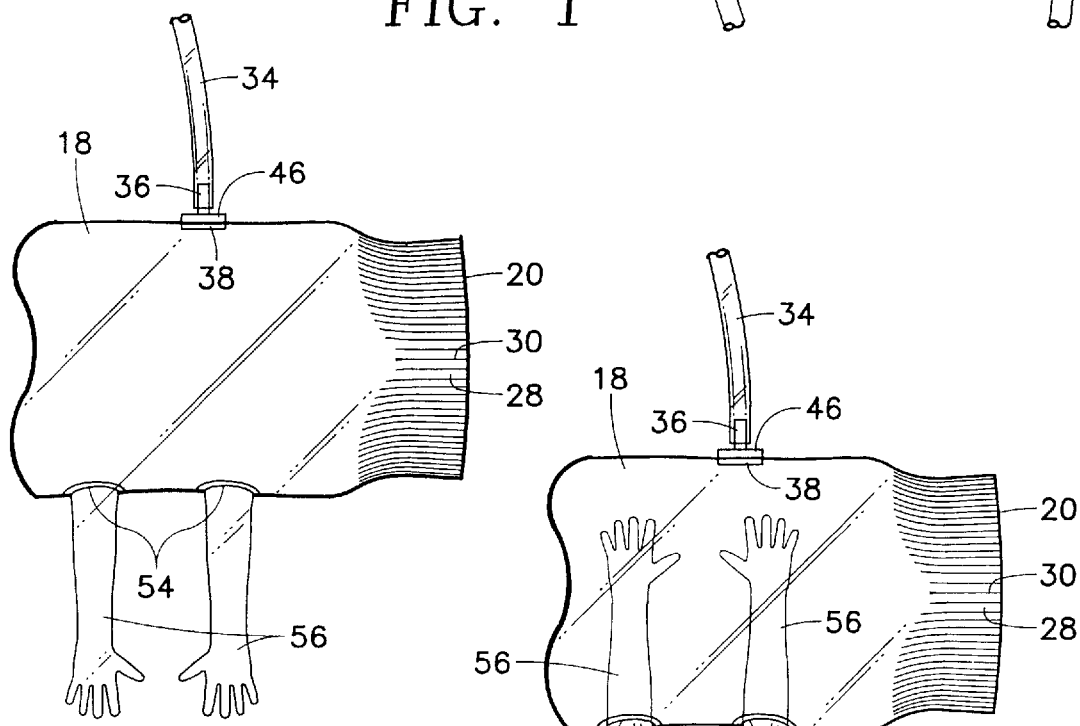
FIG. 2 is a top plan view of a portion of the hyperbaric oxygen chamber constructed in accordance with this invention wherein the chamber includes a plurality of hand access openings showing reversible tubular glove members of the hand access openings in an exterior protruding position from the chamber.

Normally with gas being supplied within the internal chamber 22 to a pressure of between one to one and one-half atmospheres, the tubular members 56 will be positioned in an outwardly protruding position from the bag 18 as shown in FIG. 2. However, upon a medical practitioner desiring to perform certain operations on the human patient 10, such as manipulating an area of the human patient's body, the medical practitioner is able to forcibly move each of the tubular members 56 to within the internal chamber 22 by inserting each of the caregiver's hands in conjunction with a tubular member 56. This will locate the caregiver's hands within the internal chamber 22 permitting the caregiver to perform the desired physical function on the human patient 10. The typical material of construction for the tubular members 56 will be thin, surgical rubber which is commonly used in the making of surgical type of gloves used in medical operations.

Figure 3:
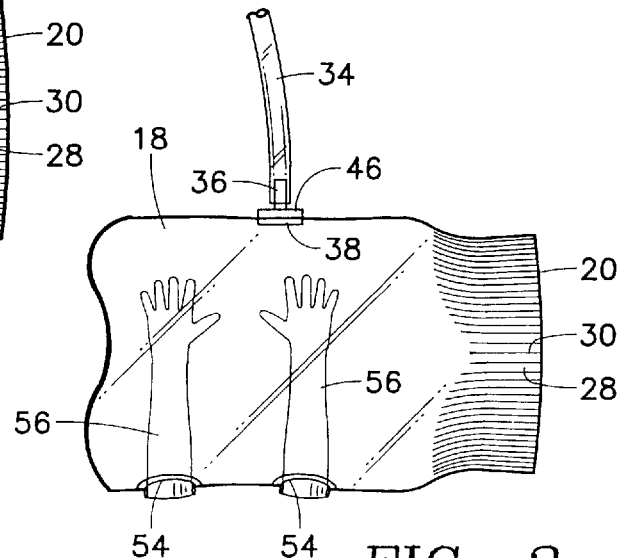
FIG. 3 is a view similar to FIG. 2 but showing the tubular glove members in the reversed position within the interior of the chamber.

When the caregiver has completed performing whatever physical operation is desired on the human patient 10, the medical practitioner is to merely withdraw his or her hands and arms from the internal chamber 22 through the respective access openings 54 which will result in the tubular members 56 again assuming the outwardly protruding position shown in FIG. 2. The usage position in conjunction with the human patient is shown in FIG. 3 of the drawings.

It is possible that the sealing tape 32 could be adjusted so tightly that very little oxygen is permitted to escape. In such a case, the sealing tape 32 would be loosened, somewhat, so that the pressure of the gas within the internal chamber 22 is maintained within a narrow window of pressure required for wound healing. Typically, the bag 18 is to be manufactured to be six to eight feet long and three to four feet wide.

It is to be restated that one of the principal features of utilizing the chamber 16 of the present invention is that when it is observed that the bag 18 is closely located against a wound the medical practitioner only needs to pull the bag 18 in an outward direction adjacent the wound creating a bulge 21. Even if this wound is located directly adjacent the sealing tape 32, bunching of the pleats 28 over the area of the wound will permit a localized expansion of the bag 18 into bulge 21. This expansion of the bag 18 into bulge 21 in the desired area is for the purpose of increasing of the volume of oxygen that comes into contact with the wound necessary to enhance healing.

Referring particularly to FIG. 7 of the drawings, there is shown a second embodiment of non-kinking connection of the oxygen supply tube 34 to the bag 18. At a corner of the bag 18, there is formed a right angled extension 58. This right angled extension 58 includes a hole 60 that closely conforms in size to the oxygen supply tube 34. The gas supply tube 34 is to be pushed through the hole 60 until the inner end 62 of the gas supply tube 34 extends about eight inches within the internal chamber 22 of the bag 18. The bag 18 must include seams at various locations. Forming of the extension 58 is to be at one of those seams 64. The locating of the gas supply tube 34 at the seam 64 further reduces the possibility of any kinking occurring. Once the gas supply tube 34 is installed in position with the inner end 62 extending about eight inches within the internal chamber 22, an appropriate sealing is to occur between the extension 58 and the oxygen supply tube 34. This type of sealing could either be by adhesive, heat sealing or even an exterior tape.

An important feature of this invention is that if the pressure level of the gas within the bag 18 is not maintained to within a certain narrow "window" at a selected pressure, the hyperbaric oxygen chamber of this invention will not be nearly as effective in healing of wounds. For all known wounds the desired range of pressure should be 0.5 to 10 millimeters of mercury (mm of Hg) above ambient pressure. This narrow window of pressure above ambient pressure is necessary to both exclude reperfusion injury and prevent oxygen toxicity. Reperfusion injury is injury which is caused by the pressure being below this narrow window pressure range, and oxygen toxicity is what occurs when the pressure level is above the range of the narrow window pressure. Within this precise range, the biological process is altered such that the development of scar tissue is retarded while at the same time blood vessel growth is accelerated. The net result of this is that less scar tissue is generated and more vascular dense, healthy tissue is laid down in the wound. These healed wounds can withstand considerably more pressure than scar tissue and consequently these healed wounds do not tend to rebreak down. Therefore, a simple but effective way must be used to make it readily apparent to the caregiver, which is usually a doctor or a nurse, that the correct amount of pressure is being maintained within the bag 18.

Figure 8:
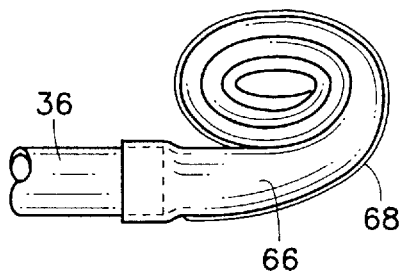
FIG. 8 is a side elevational view of a Bourdon tube type of pressure sensor that can be utilized in conjunction with a hyperbaric oxygen chamber of the present invention showing the pressure sensor in the position of detecting only a small increase in pressure above ambient pressure.
Figure 9:
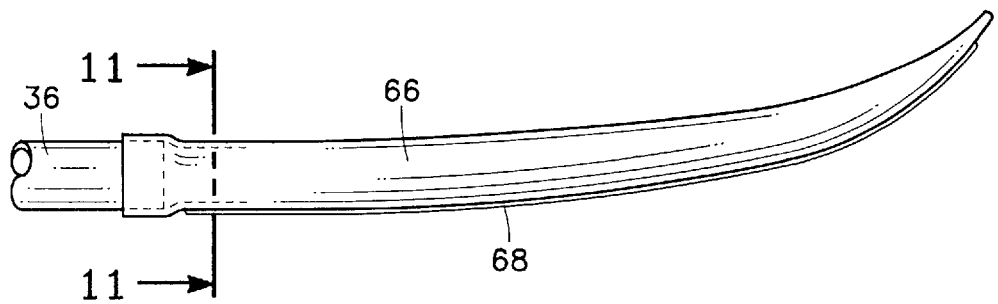
FIG. 9 is a side elevational view of the pressure sensor of FIG. 8 showing the pressure sensor in the position of detecting an excessive pressure level.
Figure 10:
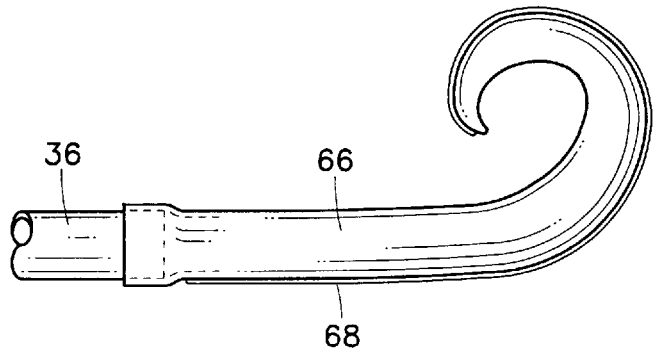
FIG. 10 is a side elevational view of the pressure sensor that is mounted in conjunction with the hyperbaric oxygen chamber of the present invention showing the pressure sensor in its correct position detecting the correct amount of pressure within the hyperbaric oxygen chamber.
Figure 11:
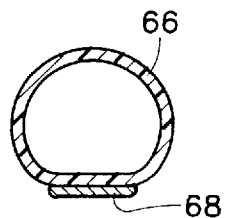
FIG. 11 is a cross-sectional view through the sensor taken along line 11—11 of FIG. 9.

Types of sensors that may be utilized in conjunction with the bag 18 are manometric, liquid crystal, silicon chip and Bourdon tube. Referring particularly to FIGS. 1, 8, 9, 10 and 11 of the drawings, there is shown a Bourdon tube type of pressure sensor incorporated with the bag 18. The Bourdon tube type comprises a spiral plastic tube 66 which is adhered on one side to a thin metal strip 68. The thin metal strip 68, when at rest, has a tendency to coil into a spiral. The single entry opening into the plastic tube 66 is mounted onto a connector stem 36 which is constructed in accordance with the structure shown in FIG. 6 of the drawings. The pressure of the gas within the bag 18 is supplied within the plastic tube 66. If the pressure is too low, the sensor will be in the position as shown in FIG. 8. If the pressure is too high, the sensor will be in the position as shown in FIG. 9. The correct position for the sensor is shown in FIGS. 1 and 10. By the caregiver making a momentary glance of the sensor, the caregiver can quickly determine if the pressure level within the bag 18 is too low, too high, or just right. It is to be understood that normally there will be incorporated a pressure regulator (not shown) on the gas supply source. It is important that whatever sensor is utilized in conjunction with the bag 18 that it be as inexpensive as possible so that the bag 18 can be manufactured to be disposable. With this thought in mind, this is why the Bourdon tube type of sensor shown in FIGS. 1, 8–11 of the drawings would be desirable because it is inherently inexpensive. Also, a silicon chip type of sensor may also be sufficiently inexpensive.

What is claimed is:

1. A portable disposable topical hyperbaric oxygen chamber for localized treatment of wounds on a portion of a body of an animal comprising:

an enclosing bag having an internal chamber, a gas, said enclosing bag to receive said gas under pressure, said gas within said enclosing bag being at a pressure greater than 0.5 millimeters of Mercury above ambient pressure but lees than 10 millimeters of Mercury, said gas including oxygen, said enclosing bag having a single body access opening to achieve entry into said internal chamber, a portion of a body of an animal is adapted to be inserted within said internal chamber with the portion of the body adapted to being conducted through said body access opening adapted to be located within said internal chamber, said enclosing bag having a wall constructed of thin, flexible, transparent material;

said wall of said bag around said body access opening including a series of preformed pleats, said access opening having an initial opening size, said preformed pleats being formed by a series of parallel spaced apart score lines formed within said wall, said preformed pleats permitting expanding of said initial opening size of said access opening as well as permitting contraction of said initial opening size of said access opening, said preformed pleats facilitating gathering of said wall at said access opening to form a close fit with the portion of the body of the animal, said preformed pleats also allowing localized changes in the shape of the bag to accommodate locations of certain wounds by concentrating the volume of oxygen over the area of the wound;

sealing means applied to said wall at maid body access opening adapted for forming a substantially airtight seal between said enclosing bag and the portion of the body permitting only slow leakage of said gas from said internal chamber; and said wall having at least one supply connector adapted to connect with a gas supply tube to supply said gas, said supply connector having a male tubular stem mounted on an enlarged flange, said enlarged flange being fixedly secured to said wall, whereby said enlarged flange prevents kinking of the gas supply tube insuring continuous supply of said gas into said internal chamber.

2. A portable disposable topical hyperbaric oxygen chamber for localized treatment of wounds on a portion of a body of an animal comprising:

an enclosing bag having an internal chamber, a gas, said enclosing bag to receive said gas under pressure, said gas within said enclosing bag being at a pressure greater than 0.5 millimeters of Mercury above ambient pressure but less than 10 millimeters of Mercury, said gas including oxygen, said enclosing bag having a single body access opening to achieve entry into said internal chamber, a portion of a body of an animal in adapted to be inserted within said internal chamber with the portion of the body adapted to being conducted through said body access opening adapted to be located within said internal chamber, said enclosing bag having a wall constructed of thin, flexible, transparent material;

said wall of said bag around said body access opening including a series of preformed pleats, said access opening having an initial opening size, said preformed pleats being formed by a series of parallel spaced apart score lines formed within said wall, said preformed pleats permitting expanding of said initial opening size of said access opening as well an permitting the contraction of said initial opening size of said access opening, said preformed pleats facilitating gathering of said wall at said access opening to form a close fit with the portion of the body of the animal, said preformed pleats, when bunched together, allowing localized shape changes to concentrate the volume of oxygen over the area of the wound;

sealing means applied to said wall at said body access opening adapted for forming a substantially airtight seal between said enclosing bag and the portion of the body permitting only slow leakage of said gas from said internal chamber; and said wall having at least one drain connector, said drain connector adapted to connect with a drain tube for removing of accumulated liquid from within said internal chamber.

3. A portable disposable topical hyperbaric oxygen chamber for localized treatment of wounds on a portion of a body of an animal comprising:

an enclosing bag having an internal chamber, a gas, said enclosing bag to receive said gas under pressure, said gas within said enclosing bag being at a pressure greater than 0.5 millimeters of Mercury above ambient pressure but less than 10 millimeters of Mercury, said gas including oxygen, said enclosing bag having a single body access opening to achieve entry into said internal chamber, a portion of a body of an animal is adapted to be inserted within said internal chamber with the portion of the body adapted to being conducted through said body access opening adopted to be located within said internal chamber, said enclosing bag having a wall constructed of thin, flexible, transparent material;

said wall of said bag around said body access opening including a series of preformed pleats, said access opening having an initial opening size, said preformed pleats being formed by a series of parallel spaced apart score lines formed within said wall, said preformed pleats permitting expanding of said initial contraction of said initial opening size of said access opening, said preformed pleats facilitating gathering of said wall at said access opening to form a close fit with the portion of the body of the animal, said preformed pleats, when bunched together, allowing localized shape changes to concentrate the volume of oxygen over the area of the wound;

sealing means applied to said wall at said body access opening adapted for forming a substantially airtight seal between said enclosing bag and the portion of the body permitting only slow leakage of said gas from said internal chamber; and at least one hand access opening formed within said wall, said hand access opening including a tubular glove member, said tubular glove member being formed of a thin, flexible, airtight material, said tubular glove member being movable between an exterior position and an interior position, said exterior position locating said tubular glove member exteriorly of said wall, said interior position locating said tubular glove member within said internal chamber, whereby a person's hand is to connect with said tubular glove member and move said tubular glove member within said internal chamber permitting the person's hand to perform functions on said portion of the body within said internal chamber while maintaining a gas pressurized environment of said gas within said internal chamber.

4. The portable pressurized hyperbaric oxygen chamber as defined in claim 3 wherein:

said wall having at least one supply connector to connect with a gas supply tube to supply said gas, said supply connector having a male tubular stem mounted on an enlarged flange, said enlarged flange being fixedly secured to said wall, whereby said enlarged flange prevents kinking of said gas supply tube insuring continuous supply of said gas through said gas supply tube into said internal chamber.

5. The portable pressurized hyperbaric oxygen chamber as defined in claim 3 wherein:

said wall having at least one drain connector, said drain connector adapted to connect with a drain tube for removing of accumulated liquid within said internal chamber.

6. The portable pressurized hyperbaric oxygen chamber as defined in claim 3 wherein:

a pressure sensor being connected to said enclosing bag, said pressure sensor being capable of denoting a narrow window of pressure level of said gas to an observer during operation of said hyperbaric oxygen chamber.

* * * * *